(12) United States Patent
Aferzon

(10) Patent No.: US 7,794,479 B2
(45) Date of Patent: Sep. 14, 2010

(54) SPINAL SUPPORT COUPLING DEVICE

(75) Inventor: Joseph Aferzon, New Britain, CT (US)

(73) Assignee: Zimmer Spine, Inc., Minneapolis, MN (US)

(*) Notice: Subject to any disclaimer, the term of this patent is extended or adjusted under 35 U.S.C. 154(b) by 1662 days.

(21) Appl. No.: 10/519,423

(22) Filed: Dec. 23, 2004

(65) Prior Publication Data

US 2005/0234449 A1    Oct. 20, 2005

Related U.S. Application Data

(60) Provisional application No. 60/394,779, filed on Jul. 10, 2002.

(51) Int. Cl.
*A61B 17/70* (2006.01)

(52) U.S. Cl. .................... 606/254; 606/86 R; 606/264; 606/279

(58) Field of Classification Search .............. 606/86 A, 606/60, 246, 250–272, 275–279, 130
See application file for complete search history.

(56) References Cited

U.S. PATENT DOCUMENTS

| | | | |
|---|---|---|---|
| 2,338,159 A * | 1/1944 | Appleton | 223/99 |
| 2,697,433 A * | 12/1954 | Zehnder | 606/96 |
| 2,774,350 A * | 12/1956 | Cleveland, Jr. | 606/54 |
| 3,299,883 A * | 1/1967 | Rubens | 600/102 |
| 6,530,929 B1 * | 3/2003 | Justis et al. | 606/103 |
| 6,709,435 B2 * | 3/2004 | Lin | 606/250 |
| 7,008,422 B2 | 3/2006 | Foley et al. | |
| 7,188,626 B2 | 3/2007 | Foley et al. | |
| 7,250,052 B2 | 7/2007 | Landry et al. | |

OTHER PUBLICATIONS

International Search Report dated Apr. 28, 2004.

* cited by examiner

*Primary Examiner*—Thomas C Barrett
*Assistant Examiner*—Christine L Nelson
(74) *Attorney, Agent, or Firm*—Crompton, Seager & Tufte, LLC

(57) ABSTRACT

The present invention is directed to a spinal support coupling device (10) comprised of first and second radial frames (44A and 44B), each pivotably coupled to a center pivot hinge (30). A traveling arm (20) is provided, coupled to the first and second radial frames (44A and 44B) at the center pivot hinge (30). The traveling arm (20) is configured to rotate with respect to the first and second radial frames (44A and 44B) around the center pivot hinge (30). A coupling rod (80) is attached to the traveling arm (20) and configured to connect a first and a second surgical screw (60A and 60B), placed into a patient. The first and second radial frames (44A and 4413) are configured to retain corresponding first and second extension rods (64A and 64B), extending away from the top of the first and second surgical screws (60A and 60B).

37 Claims, 7 Drawing Sheets

SPINAL SUPPORT COUPLING DEVICE

RELATED APPLICATION

This application claims priority to U.S. Provisional Application No. 60/394,779, filed on Jul. 10, 2002, the entirety of which is incorporated herein by reference.

FIELD OF INVENTION

This invention relates to a spinal support coupling device. More specifically, the present invention relates to a spinal support coupling device for use in inserting coupling rods between screws inserted into a patient's spine.

BACKGROUND OF INVENTION

Support devices, utilized in spinal surgery, often include screws driven through the bones in the spinal column. The screws are subsequently connected by way of a metal rod or a plate after the screws have been inserted. These rods or plates are typically inserted through the screw heads, having complex mechanical connections, allowing for variable fixation angles. This approach, using variable angle screw heads, requires the heads to align to accommodate for an arc of a pre-defined radius. This enables the delivery of the connecting rod, shaped as an arc or a circle, with the same radius.

However, there are a number of shortcomings with such systems. For example, both screw heads have to be able to pivot to adjust for the fixed trajectory of the connecting rod. Additionally, because the extensions from the screws need to be secured to the device at a single point, there is limited flexibility when positioning the device, making it more difficult to set up. Furthermore, because the prior art devices require that the screw extensions meet at a single point, manipulation of the screw heads and connecting rods involves more movement under the patient's skin and muscle, requiring substantially higher surgical skills and experience as well as a larger surgical incision through the patients back muscles, relative to currently practiced methods for such surgeries.

SUMMARY OF INVENTION

The present invention looks to overcome the drawbacks associated with the prior art by providing a more flexible means to connect the surgery device to the screws, limiting the size of the incision required and making manipulation of the screws and connecting rod easier for the surgeon.

To this end, in one embodiment of the present invention, a spinal support coupling device is provided comprised of first and second radial frames, each pivotably coupled to a center pivot hinge. A traveling arm is provided, coupled to the first and second radial frames at the center pivot hinge. The traveling arm is configured to rotate with respect to the first and second radial frames around the center pivot hinge.

A coupling rod is attached to the traveling arm and configured to connect a first and a second surgical screw, placed into a patient. The first and second radial frames are configured to retain corresponding first and second extension rods, extending away from the top of the first and second surgical screws.

BRIEF DESCRIPTION OF THE DRAWINGS

The present invention will be further understood from the following description with reference to the accompanying drawings, in which.

DETAILED DESCRIPTION

The present invention comprises a spinal support coupling device 10. In one embodiment, as illustrated in FIG. 1, coupling device 10 is comprised principally of a traveling arm 20, a center pivot hinge 30 and first and second radial frames 44A and 44D.

Figure 1:
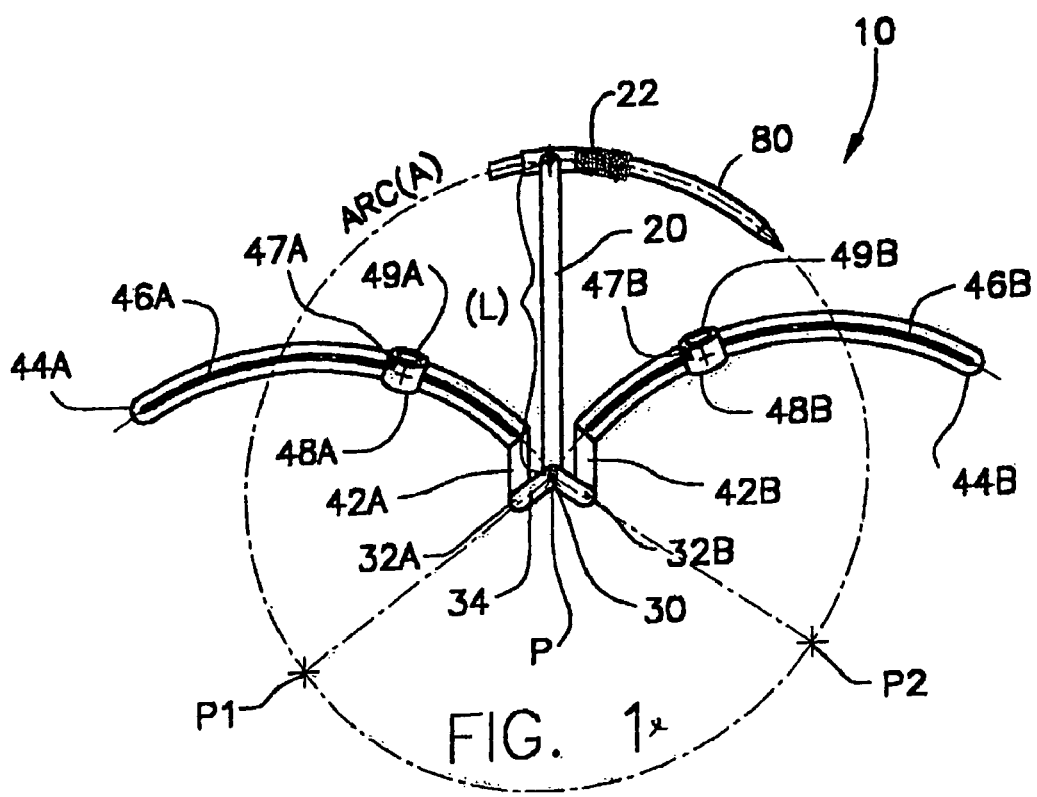
FIG. 1 is a front view of a spinal support coupling device, in accordance with one embodiment of the present invention.

As illustrated in FIG. 1, traveling arm 20 is of a particular length (L) and maintains a piercing arm 22 mounted at the top. Piercing arm 22, attached perpendicularly at the top of traveling arm 20, preferably has a curvature with a radius (L), and is extended along arc (A), defined by a circle with radius (L). The bottom portion of traveling arm 20, distal to piercing arm 22, is attached to a center pivot hinge 30 at a center point (P).

In an alternative arrangement, piercing arm 22 may maintain a different shape that does not have a curvature with a radius (L) that corresponds to the length of traveling arm 20, or extend along arc (A). For example, piercing arm 22, may be configured as a straight bar, a v-shaped bar, or even a curved bar with curvature having a radius other than (L).

Additional alternative arrangements may include a piercing arm 22 attached to traveling arm 20 such that piercing arm 22 extends forward either in a line, tangent to the curve having a radius of (L), or it may be aimed along an arc (A) of a circle having a radius (L). Any shaped piercing arm 22, attached to traveling arm 20 in substantially the same direction, for use in a similar coupling device 10, is within the contemplation of the present invention.

As illustrated in FIG. 1, a coupling rod 80 is removably attached to the end of piercing arm 22. The length of coupling rod 80 is preferably roughly equal to the distance between two vertebrae on a patient's back, which need to be anchored together. Coupling rod 80, attached to the end of piercing arm 22, preferably has a curvature with a radius (L), and is extended along arc (A), defined by the circle with a radius (L). The front portion of coupling rod 80 is tapered so as to allow easier movement inside of the patient.

In an alternative arrangement, coupling rod 80 may maintain a different shape that does not have a curvature with a radius (L) or extend along arc (A). For example, coupling rod 80, may be configured as a straight bar, a v-shaped bar, or even a curved bar with curvature having a radius other than (L). The shape of coupling rod 80 may vary, depending on the shape of the particular vertebrae to be connected.

For the purposes of illustration, the preferred shapes of coupling rod 80 and piercing arm 22, with curvatures with a radius (L), extended along arc (A), defined by the circle with a radius (L), are used throughout.

As illustrated in FIG. 1, center pivot hinge 30, attached to traveling arm 20, is coupled to first and second center pivot hinge connecting arms 32A and 32B. First and second center pivot hinge connecting arms 32A and 32B preferably extend downwardly at an angle from center pivot hinge 30 as described in more detail below, although the invention is not limited in this respect. For example, in another embodiment of the invention, pivot hinge connecting arms 32A and 32B extend at variable angles from center pivot hinge 30, including angles in an upward direction, where the angles at which connecting arms 32A and 32B extending from pivot hinge 30 may be the same or different from each other.

First and second radial frame connection arms 42A and 42B attached to connecting arms 32A and 32B respectively and preferably extend away from first and second center pivot hinge connecting arms 32A and 32B, from points distal to center pivot hinge 30.

First and second radial frames 44A and 44B are preferably attached at the ends of radial frame connecting arms 42A and 42B respectively, at points distal to center pivot hinge connecting arms 32A and 32B. Radial frames 44A and 44B extend radially from radial frame connection arms 42A and 42B with a curvature preferably having a radius (L), corresponding to the length of traveling arm 20, which extends along an arc (A), defined by the circle with a radius (L). In this configuration, radial frames 44A and 44B that are attached to center pivot hinge 30 via connecting arms 32A, 32B, 42A and 42B, such that circles, having arcs (A), drawn through both first and second radial frames 44A and 44B, would intersect at center point (P), located at center pivot hinge 30.

The formation and connections between center pivot hinge 30, first and second pivot hinge connecting arms 32A and 32B, first and second radial frame connecting arms 42A and 42B and radial frames 44A and 44B can be set in several different arrangements while still maintaining the proper function of device 10.

For example, in a first preferred configuration, pivot hinge connecting arms 32A and 32B are independently attached to center pivot hinge 30 so as to be independently movable with respect to one another. In this arrangement, the angle between first pivot hinge connecting arm 32A and second pivot hinge connecting arm 32B may vary based on how device 10 is ultimately connected to the patient.

It is noted that the above described configuration is the preferable configuration for first and second pivot hinge connecting arms 32A and 32B. However, this is in no way intended to limit the scope of the present invention. Several other alternative configurations of first and second pivot hinge connecting arms 32A and 32B, are with in the contemplation of the present invention.

For example, in an alternative arrangement, first and second pivot hinge connecting arms 32A and 32B, may be in a fixed angle relative to one another. Likewise, first and second pivot hinge connecting arms 32A and 32B, may be in an arrangement where the there are a series of predefined angles between the two, such that the angle between first pivot hinge connecting arm 32A and the traveling arm 20 is always correspondent with the angle between second pivot hinge connecting arm 32B and the traveling arm 20.

In addition to the arrangements regarding the connection of first and second pivot hinge connecting arms 32A and 32B with center pivot hinge 30, various arrangements concerning the connection of first and second pivot hinge connecting arms 32A and 32B with first and second radial frame connecting arms 42A and 42B and radial frames 44A and 44B are also with in the contemplation of the present invention.

For example, center pivot hinge connecting arms 32A and 32B and radial frame connection arms 42A and 42B can also either be formed as four hingedly attached individual elements or they can be formed as two separate fixedly attached portions consisting of connecting arms 32A and 42A and connecting arms 32B and 42B. In the form of hingedly attached elements, the angles between center pivot hinge connecting arms 32A and 32B may vary, with respect to radial frame connection arms 42A and 42B. In the form of fixedly attached elements, the angles between center pivot hinge connecting arms 32A and 32B remains constant, with respect to radial frame connection arms 42A and 42B.

Furthermore, radial frames 44A and 44B may either connect fixedly or hingedly to first and second radial frame connection arms 42A and 42B. In the form of a hinged connection, radial frames 44A and 44B may maintain varying angles with respect to first and second radial frame connecting arms 42A and 42B. Alternatively, when formed as a fixed connection, radial frame connection arms 42A and 42B and radial frames 44A and 44B maintain a constant angle with respect to one another.

In one embodiment each radial frame connecting arm 42A, radial frame 44A and pivot hinge connecting arm 32A may be formed as an integrated assembly. Likewise, radial frame connecting arm 42B, radial frame 44B and pivot hinge connecting arm 32B may also be formed similarly. These two assemblies are then hingedly attached to center pivot hinge 30 at center point (P).

Irrespective of the connectivity arrangements between these elements, as illustrated in FIG. 1, a line drawn from center point (P) at center hinge 30 to the points (P1) and (P2), preferably runs along the longitudinal axes of pivot hinge connecting arms 32A and 32B. Thus, in the preferred configuration, the angles between pivot hinge connecting arms 32A and 32B extending away from center pivot hinge 30 is equal to the angle formed at the top of the triangle formed between center point (P) and coupling rod 80 connection points (P1) and (P2).

It is also noted that the varying manners of connection and angles between connecting arms 32A, 32B, 42A and 42B and radial frames 44A and 44B are all within the contemplation of the present invention. Regardless of the manner of formation however, in order for proper operation of coupling device 10, radial frames 44A and 44B advantageously maintain curvatures having a radius (L), which extend along arc (A), defined by the circle with a radius (L), such that their intersection point always falls at center point (P) at center pivot hinge 30.

In fact, in accordance with one embodiment of the present invention, it is further contemplated that coupling device 10 may be formed without connecting arms 32 and 42 so that radial frames 44 hingedly attach directly to center pivot hinge 30.

For the purposes of describing the salient features of the present invention, center pivot hinge connecting arms 32A and 32B are shown as independently pivotable about center point hinge 30. Radial frame connecting arms 42A and 42B and radial frames 44A and 44B are described as fixedly connected.

In one embodiment each radial frame connecting arm 42A, radial frame 44A and pivot hinge connecting arm 32A may be formed as an integrated assembly. Likewise, radial frame connecting arm 42B, radial frame 44B and pivot hinge connecting arm 32B may also be formed similarly. The two assemblies are then hingedly attached to center pivot hinge 30 at center point (P).

As illustrated in FIG. 1, first and second radial frames 44A and 44B, each maintain tracks 46A and 46B respectively. Tracks 46A and 46B are preferably disposed in the center of radial frames 44A and 44B, however, they alternatively may be formed towards either the upper or lower edges as necessary. Tracks 46A and 46B may be any type of track such as a slot, recessed groove or retaining flange. Likewise, tracks 46A and 46B may be located on either face of radial frames 44A and 44B or even pass entirely through the frames. Any configuration, of tracks, capable of carrying out the desired function of tracks 46A and 46B as described below is within the contemplation of the present invention.

Positioned within each track 46A and 46B, sliding retainers 48A and 48B are slidingly mounted, capable of movement across the entire length of radial frames 44A and 44B.

Sliding retainers 48A and 48B are preferably fashioned as cylindrical connectors, attached to tracks 46A and 46B respectively. Each sliding retainer includes a connection bore such as 49A and 49B, through which extension rods or other cylindrical extensions can pass through. It is further contemplated that sliding retainers 48A and 48B maintain a locking mechanism such as 47A and 47B, that can engage in a locking position when a rod or other cylinder is placed within, preventing any further movement of the rod within the bores. Locking mechanisms 47A and 47B may operate in a screw/notch or contracting sleeve arrangement or any other arrangement capable of retarding movement of a rod with sliding retainers, such as sliding retainers 48A and 48B.

In one embodiment of the present invention, sliding retainers 48A and 48B are mounted in a way as to allow movement across the entire length of radial frames 44A and 44B respectively. It is also contemplated in the present invention that sliding retainers 48A and 48B may employ various forms of connection with tracks 46A and 46B. For example, sliding retainers 48A and 48B may be mounted so that their movement is at a fixed angle across tracks 46 or they can be mounted so as to allow a pivoting movement in addition to movement along tracks 46.

In a first example, sliding retainers 48A and 48B are positioned in a fixed angle with respect to tracks 46. For example, as illustrated in FIG. 1, at any point along radial frames 44A and 44B, sliding retainers 48A and 48B are disposed so that a line, extending through connections bores 49A and 49B, is perpendicular to line tangent to that location along the arc (A) of radial frames 44A and 44B, as illustrated in FIG. 1. It should be noted that fixed angles, other than perpendicular to the tangent line, may be used for connection bores 49A and 49B of sliding retainers 48A and 48B is also in the contemplation of the present invention.

Figure 3:
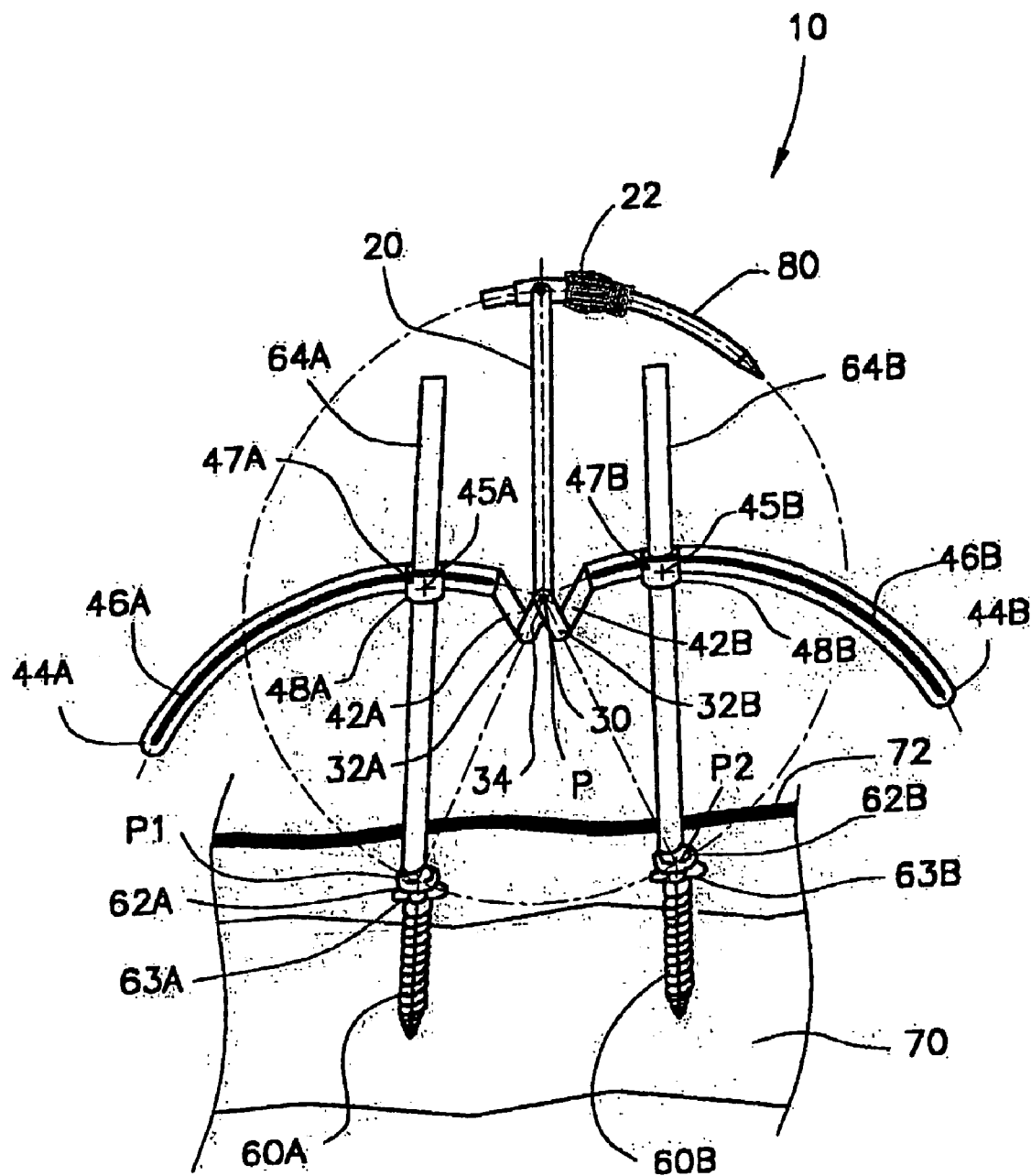
FIG. 3 is a side view of a spinal support coupling device from FIG. 1, mounted on extensions rods, in accordance with one embodiment of the present invention.

In the second example, sliding retainers 48A and 48B are mounted in a way as to allow movement across the entire length of radial frames 44A and 44B respectively. Sliding retainers 48A and 48B are pivotable on pivot axes 45A and 45B where they connect with radial frames 44A and 44B. Thus, sliding retainers 48A and 48B may be rotated about pivot axes 45A and 45B with respect to tracks 46A and 46B so as to accept extension rods or other cylinders that enter connection bores 49A and 49B from varying angles, as illustrated in FIG. 3.

It is noted that the various components of coupling device 10 may be constructed of any number of different materials such as surgical steel, titanium and rigid polyurethane or plastics. However, this list is in no way intended to limit the scope of the present invention. Coupling devices 10 constructed of any metal or other surgical grade material having similar components is within the contemplation of the present invention as well as a variety of other matters.

Figure 2:
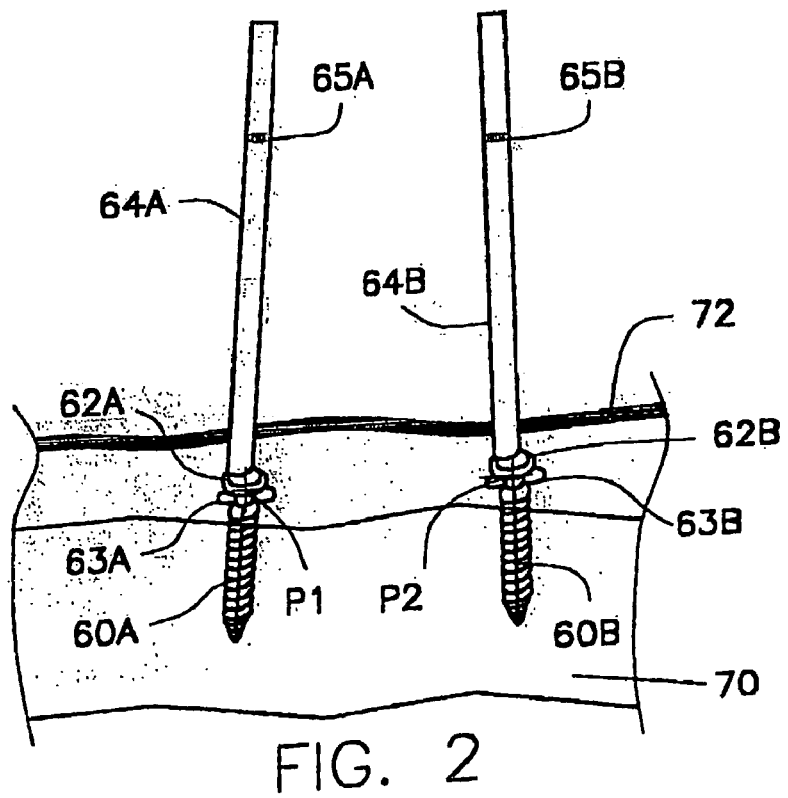
FIG. 2 is a front view of surgical screws and extension rods fixed in a patient's back, in accordance with one embodiment of the present invention.

During operation, as illustrated in FIG. 2, surgical screws 60A and 60B are inserted below the skin 72 into the spine 70 of a patient. Surgical screws 60A and 60B each have head portions 62A and 62B respectively, configured to accept a coupling rod 80 for the purpose of supporting/connecting a first vertebrae to a second vertebrae in spine 70.

Figure 4:
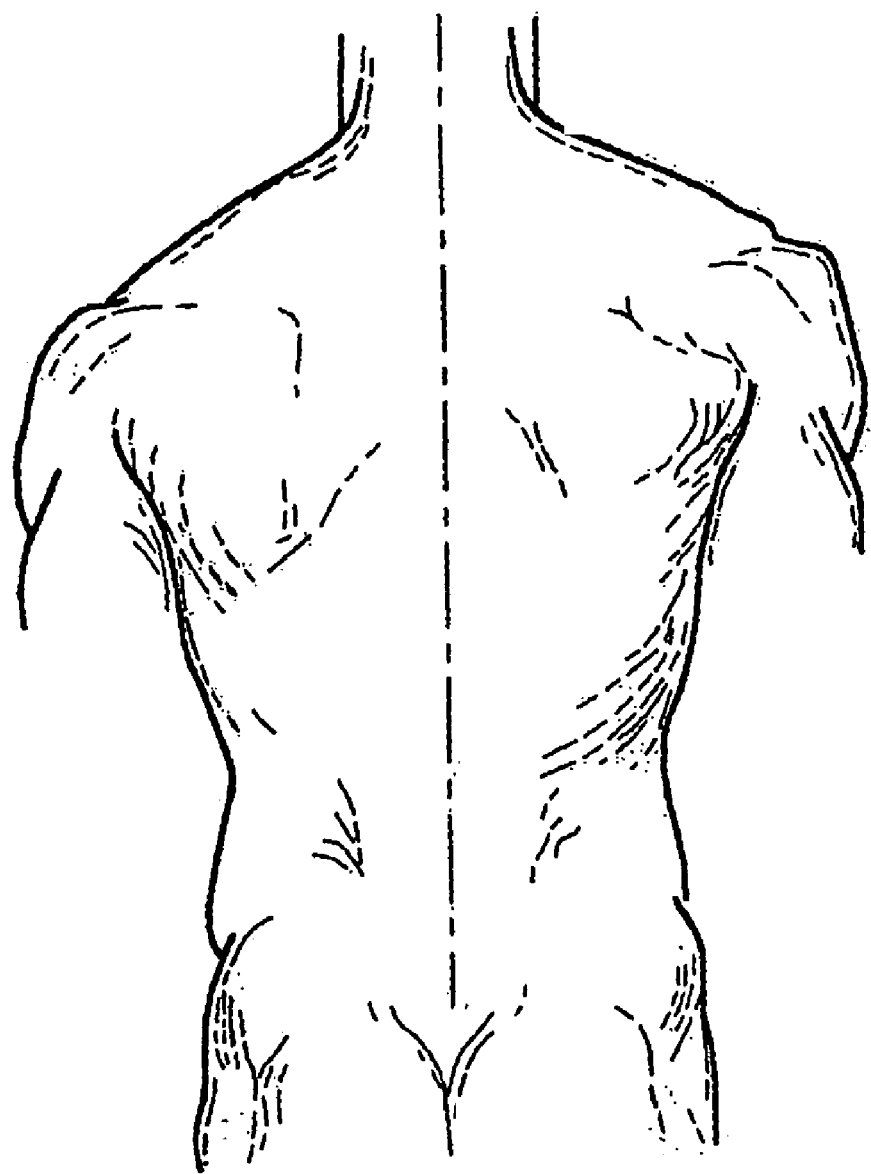
FIG. 4 is an illustration of a patient's back, wherein the spinal support coupling device may be used in accordance with one embodiment of the present invention.

Once coupling device 10 is readied, the patient is prepared for surgery and placed lying down on to a surgical table with the patient's back exposed to the surgeon as illustrated in FIG. 4. In such surgeries for the connection of two vertebrae, it is necessary to locate the affected vertebrae and identify the appropriate positions to place surgical screws 60A and 60B.

Using x-ray and other techniques, the pedicle of the affected vertebrae is located and drilling points are identified. These two points mark the location, where surgical screws 60A and 60B will eventually be'placed.

After the drilling have been identified, an incision is made in the patients back near the two vertebrae to be coupled. The initial incision through the skin and back muscle is small, allowing for a guide wire 90, illustrated in FIG. 5A, to be placed within down to the affected vertebrae. Using fluoroscopy or other similar techniques, the positioning of the guide wire 90 may be verified to ascertain that the initial taps for drilling surgical screws 60A and 60B are properly located.

After guide wire 90 is in place through the skin and muscle, a guide channel 92 is formed so as to allow room for the drilling of surgical screws 60A and 60B. After the incision is made, and guide channel 92 is in place, a series of expanders are used to enlarge guide channel 92 to the appropriate width for drilling surgical screws 60. This is done in this manner so as to limit the incision to the smallest possible size necessary to perform the procedure.

Figure 5A:
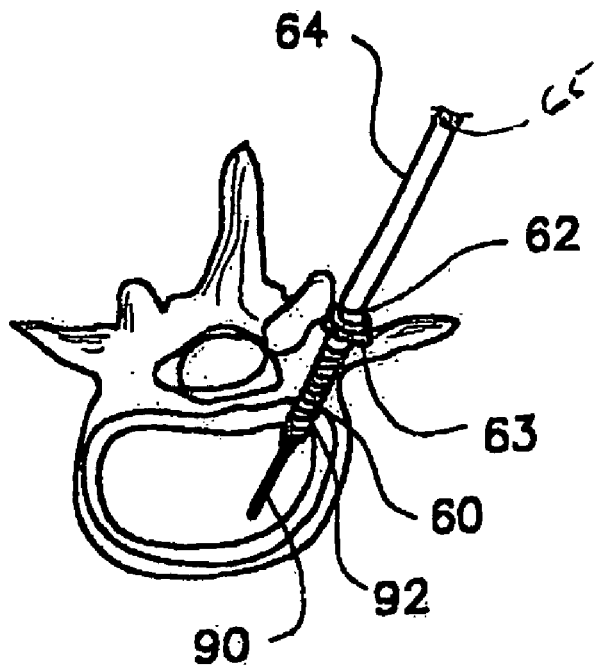
FIG. 5A is a cut-away close-up view of a surgical screw and extension rod being inserted into a patient's vertebrae, in accordance with one embodiment of the present invention.
Figure 5B:
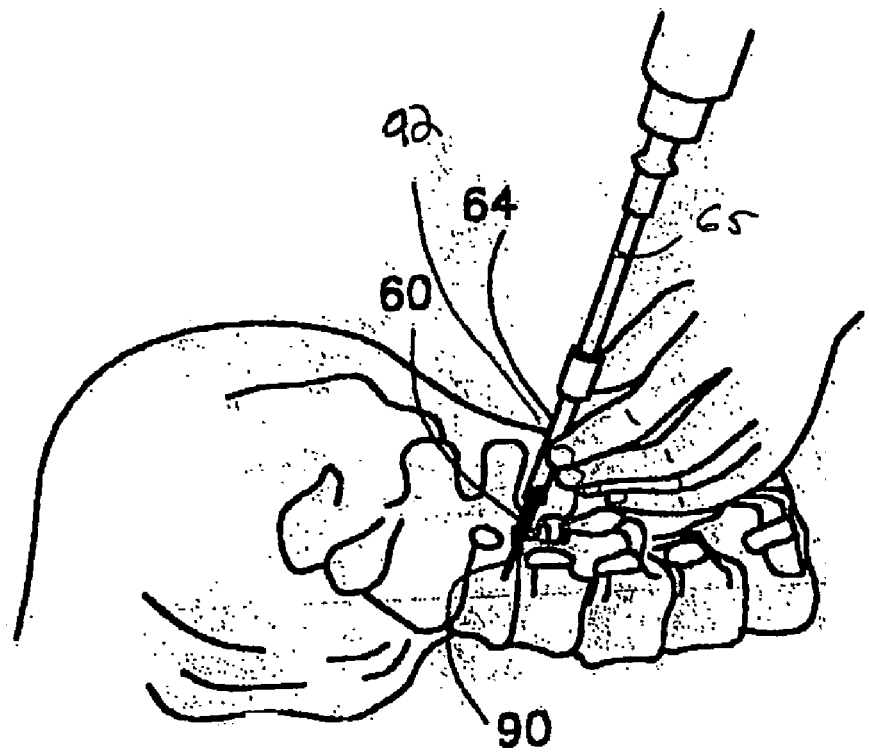
FIG. 5B is a side view of a surgical screw and extension rod being inserted into the patient's vertebrae, in accordance with one embodiment of the present invention.

As illustrated in FIG. 5B, after guide channel 92 is formed to the appropriate width, the tip of surgical screws 60 are lowered though guide channel 92 along guide wire 90 down to the affected vertebrae to be drilled. As illustrated in FIG. 5A, the placement of surgical screws 60 is done at an angle into the pedicle of each vertebra at the drilling points so as to gain maximum anchorage. This process is repeated for both surgical screws 60. When the drill is removed, extensions arms 64A and 64B are left attached to screw heads 62A and 62B.

Figure 6:
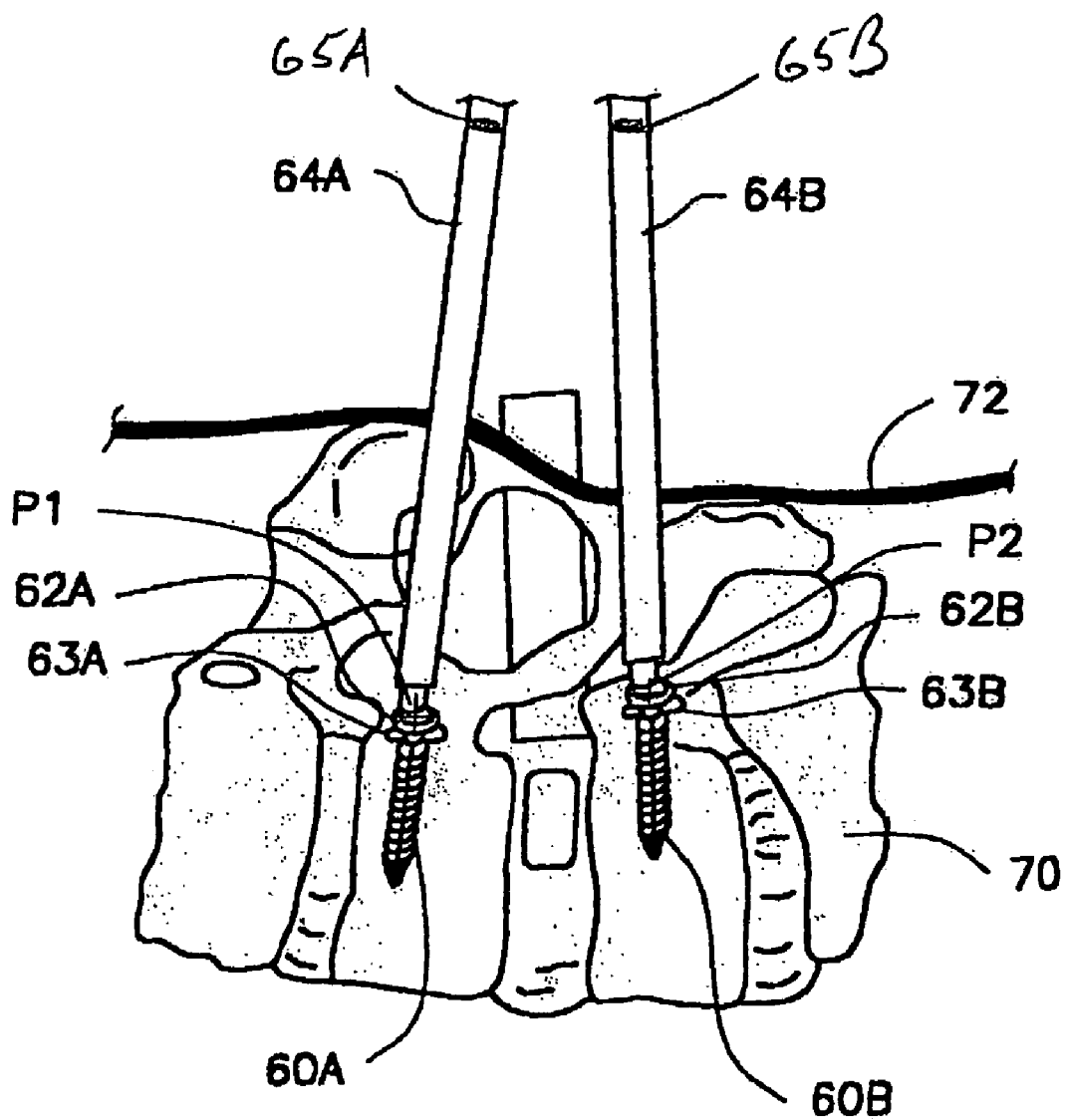
FIG. 6 is a side view of surgical screws and extension rods fixed in a patient's back, in accordance with one embodiment of the present invention.

Thus, in one embodiment of the present invention as illustrated in FIG. 6, the patient is prepared to have the two affected vertebrae connected to one another using coupling device 10. Surgical screws 60A and 60B are each drilled into their respective vertebrae at the identified points with extension rods 64A and 64B, described in more detail below, each extending upwardly from spine 70, through skin 72.

Surgical screws 60A and 60B each maintain removable extension rods 64A and 64B, attached to screw heads 62A and 62B respectively, configured to extend upwardly away from spine 70 and out through skin 72.

Screw heads 62A and 62B maintain linking bores 63A and 63B allowing for connection of surgical screws 60A and 60B by a coupling rod 80 or another similar device. Screw heads 62 with linking bores 63 may be fixed in position relative to surgical screws 60 or they may be free to swivel to allow for better angles with which to accept any connecting rods or devices.

Because extension rods 64A and 64B are attached to surgical screws 60A and 60B, via screw heads 62A and 62B, they may either be in a fixed arrangement or in a moveable arrangement. In the first arrangement, where screw heads 62A and 62B are fixed, extension rods 64A and 64B are also fixed such that they extend away from surgical screws 60A and 60B along the screws' longitudinal axes. In the second arrangement, where screw heads 62A and 62B are moveable with relation to surgical screws 60A and 60B, extension rods 64A and 64B likewise extend away from surgical screws 60A and 60B along the screws' longitudinal axes, but are free to be moved to some extent so as to allow better connection angles with sliding retainers 48A and 48B.

In one embodiment of the present invention, as illustrated in FIG. 2, extensions rods 64A and 64B each maintain distance markers 65A and 65B. Distance markers 65 are positioned along extensions rods 64A and 64B at distance (L) away from screw bores 63A and 63B. Thus, distance markers 65A and 65B are poisoned at a distance from screw bores 63A and 63B equal to the length (L) of traveling arm 20. Distance markers 65A and 65B are located at this position to mark the point, along extension rods 64A and 64B, at which radial frames 44A and 44B should be located in order for coupling rod 80, to properly align itself with screw bores 63A and 63B as discussed in more detail below.

It should be noted that the components of surgical screws 60A and 60B may be constructed of any number of different materials such as surgical steel, titanium, rigid polyurethane or plastics or any other surgical grade material.

In one embodiment of the present invention, as illustrated in FIG. 3, coupling device 10 is attached to extension rods 64A and 64B. In this process, sliding retainers 48A and 48B are positioned along tracks 46A and 46B so that they align with extension rods 64A and 64B respectively.

As discussed above, there are several variations in the mobility of sliding retainers 48A and 48B as well as in extension rods 64A and 64B. As such, there are different manners in which coupling device 10 to extension rods 64A and 64B as discussed below.

In a first arrangement, where extension rods 64A and 6413 are mounted on pivotable screw heads 62A and 62B, and where sliding retainers 48A and 48B are not pivotable in tracks 46A and 46B, extension rods 64A and 64B are moved away from the axes of surgical screws 60 so that they may properly align with connection bores 49A and 49B of sliding retainers 48.

In a second arrangement, where extension rods 64A and 64B are mounted on fixed screw heads 62A and 62B, and where sliding retainers 48A and 48B are pivotable on pivot axes 45A and 45B in tracks 46A and 46B, sliding retainers 48A and 48B are moved along tracks 46A and 46B and pivoted on pivot axes 45A and 45B so that connection bores 49A and 49B are able to slide over the tops of extension rods 64A and 64B, as illustrated in FIG. 3.

It is noted that additional arrangements may be available such as where both extensions rods 64 and sliding retainers 48 are either pivotable or fixed. However, for the purposes of illustrating the salient features of the present invention, an arrangement where extension rods 64A and 64B are fixed and where sliding retainers 48A and 48B are pivotable is described throughout.

In either case, as illustrated in FIG. 3, coupling device 10, is lowered down extension rods 64A and 64B, allowing the excess material to pass through sliding connectors 48 A and 48B. Coupling device 10 is lowered along extension rods 64A and 64B until the center point of sliding retainers 48A and 48B meets distance markers 65A and 65B, respectively, each at a distance (L), equal to the length of traveling arm 20, at which point locking mechanisms 47A and 47B secure coupling device 10 in place. It is noted that, as described above, when device 10 is in position, lines drawn from center point (P) at hinge 30 to points (P1) and (P2) at screw bores 63A and 63B, pass through the longitudinal axes of pivot hinge connecting arms 32A and 32B.

Figure 7:
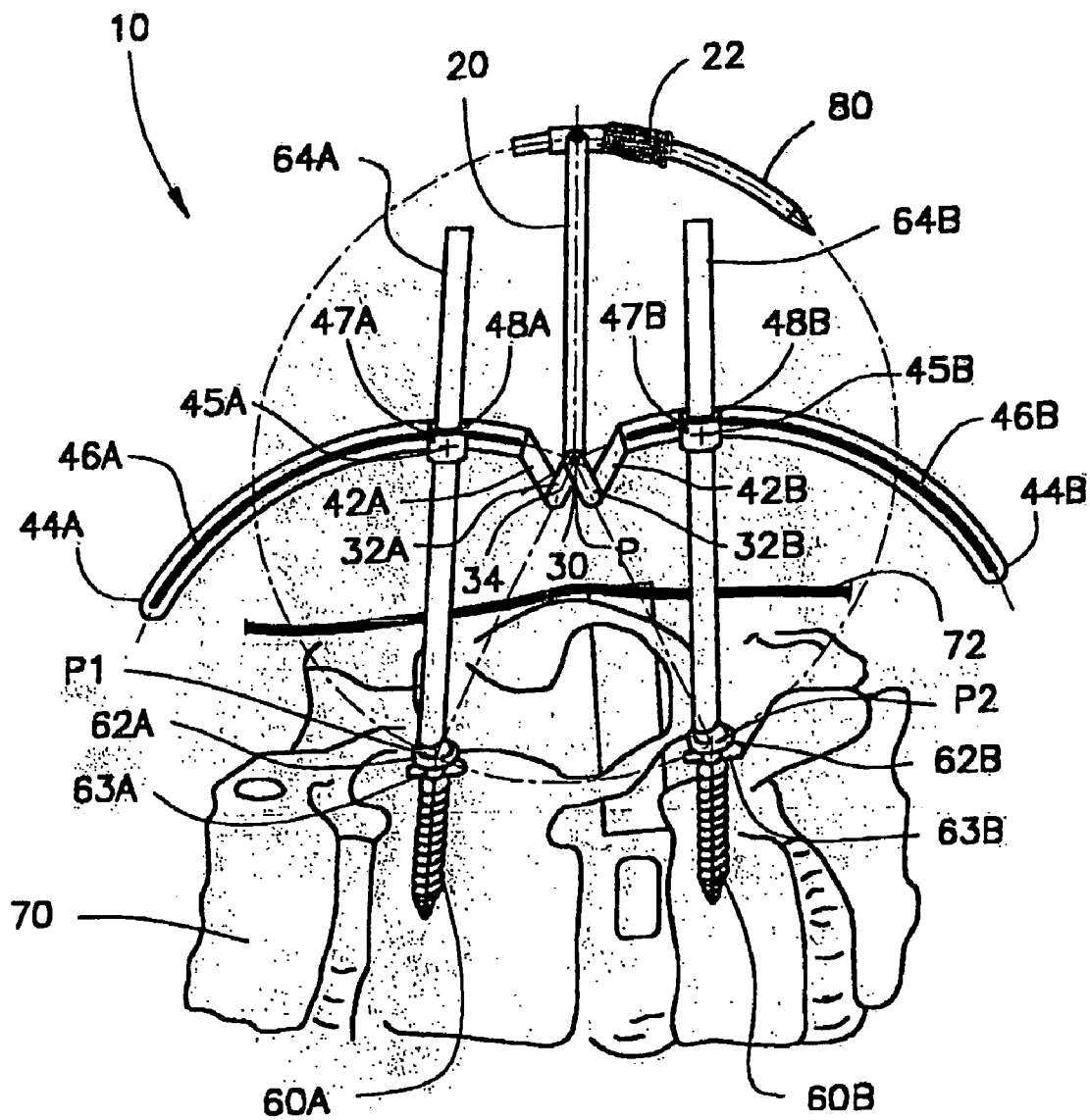
FIG. 7 is a side view of a spinal support coupling device from FIG. 1, mounted on extensions rods extending from a patient's spine, in accordance with one embodiment of the present invention.

Thus, as illustrated in FIG. 7, coupling device 10 is shown in position for operation. Coupling device 10 is mounted on extension rods 64A and 64B at a distance (L) from each screw head 62A and 62B. In this configuration, coupling device 10 is positioned to properly connect surgical screw 60A to surgical screw 60B.

In this respect, a circle, drawn around the top of each of surgical screws 60A and 60B at screw bores 63A and 63B, at points (P1) and (P2) respectively, having a radius (L), would intersect at center point (P) located at center point hinge 30. These circle would each run through the arc (a) of each of the radial frames 44A and 44B respectively.

As such, points (P), the center point, (P1), the screw bore 63A location, (P2), the screw bore 63B location, define a plane in which the connection point of surgical screw heads 62A and 62B reside with the center of coupling device 10.

Figure 8:
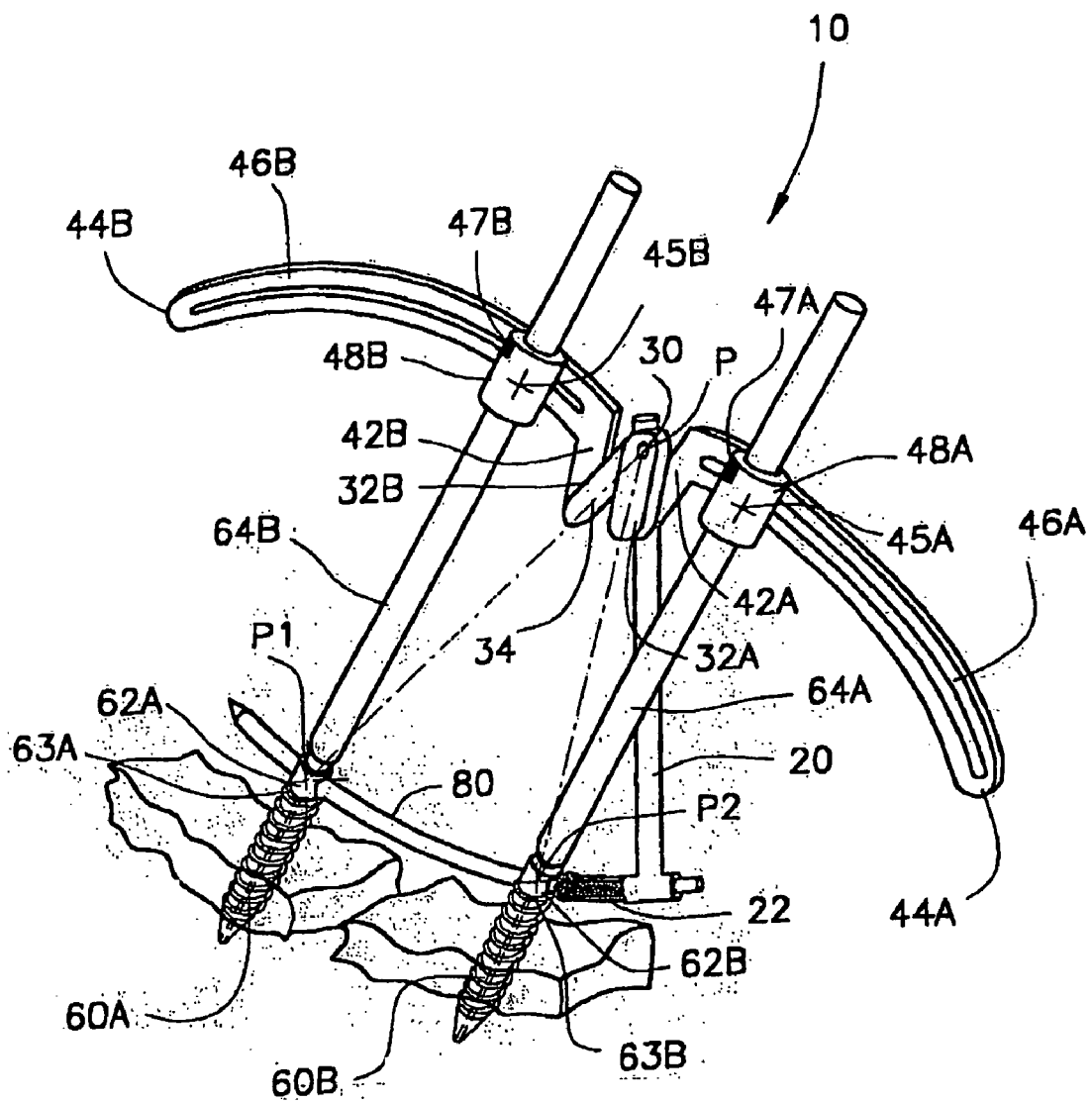
FIG. 8 is a side view of a spinal support coupling device from FIG. 1, mounted on extension rods extending from a patient's spine, in accordance with one embodiment of the present invention.

Furthermore, in this configuration, piercing arm 22, moving in a circle about center point hinge 30, travels in a circle of a radius (L) in the same plane as points (P), (P1) and (P2) and thus, always passes through points (P1) and (P2), As described below, piercing arm 22 when traveling in this circle around center point hinge 30, is in the proper plane to insert coupling rod 80 and connect surgical screw 60A to surgical screw 60B. As illustrated in FIG. 8, traveling arm 20 is swung down towards surgical screws 60A and 60B, such that piercing arm 22 enters the patient's body and moves first through screw head 62B and next through screw head 62A. Attached to the front of piercing arm 22 is a coupling rod 80 which is moved simultaneously moved through bores 63A and 63B of screw heads 62A and 62B, thus connecting surgical screws 60A and 60B.

After coupling rod 80 is in place, it is fixed in place by further tightening of screw heads 62A and 62B or any other typical connection process. Traveling arm 20 and piercing arm 22 are then removed backwards, swinging around center pivot hinge 30 and leaving coupling rod 80 in place. Extension rods 64A and 64B are then removed from surgical screws 60A and 60B and the patient's incision is closed. Coupling device 10 is uncoupled from extension rods 64A and 64B and prepared for the next surgery.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A spinal support coupling device comprising:
   first and second radial frames, each pivotably coupled to a center pivot hinge;
   a traveling arm, coupled to said first and second radial frames at said center pivot hinge, wherein said traveling arm is configured to rotate with respect to said first and second radial frames around said center pivot hinge;
   a coupling rod attached to said traveling arm and configured to connect a first and a second surgical screw, placed into a patient, wherein said first and second radial frames are configured to retain corresponding first and second extension rods, extending away from the top of said first and second surgical screws; and first and second pivot hinge connecting arms coupled to said center pivot hinge and first and second radial frame connecting arms, each coupled to a corresponding one of said pivot hinge connecting arms, and to said corresponding radial frames.

2. A spinal support coupling device as claimed in claim 1, wherein said first and second surgical screws each further maintain a bore hole located at coupling rod connection points (P1) and (P2) respectively.

3. A spinal support coupling device as claimed in claim 2, wherein said first and second surgical screws further maintain first and second screw heads respectively.

4. A spinal support coupling device as claimed in claim 3, wherein said first and second extensions rods are coupled to said first and second surgical screws via said first and second screw heads.

5. A spinal support coupling device as claimed in claim 4, wherein said traveling arm is of length (L) and wherein said first and second radial frames are curved such that they lie within an arc defined by a circle with a radius (L).

6. A spinal support coupling device as claimed in claim 5, wherein said first and second radial frames are curved such that the curvature of said radial frames is equal to the curvature of a circle having a radius (L).

7. A spinal support coupling device as claimed in claim 6, wherein first and second radial frames extend along two arcs having a radius of (L), wherein said two arcs intersect at said center pivot hinge.

8. A spinal support coupling device as claimed in claim 7, wherein said first and second radial frames each maintain tracks, configured to span a substantial length of said first and second radial frames.

9. A spinal support coupling device as claimed in claim 8, wherein said spinal support coupling device further maintains first and second sliding retainers, disposed in said tracks of said first and second radial frames respectively.

10. A spinal support coupling device as claimed in claim 9, wherein said first and second sliding retainers each maintain connection bores, configured to receive said first and second extensions rods.

11. A spinal support coupling device as claimed in claim 10, wherein said first and second sliding retainers each maintain a locking mechanism for securing said first and second extension rods within said connection bores.

12. A spinal support coupling device as claimed in claim 11, wherein said first and second sliding retainers are moveably secured in said tracks in a non-rotatable manner.

13. A spinal support coupling device as claimed in claim 12, wherein said first and second screw heads are pivotable, allowing said attached first and second extension rods to move, relative to the longitudinal axes of said first and second surgical screws, so as to facilitate connection with said first and second non-rotatable sliding retainers.

14. A spinal support coupling device as claimed in claim 11, wherein said first and second sliding retainers are moveably secured in said tracks in a rotatable manner such that said connection bores pivot.

15. A spinal support coupling device as claimed in claim 14, wherein said first and second screw heads are fixed in position, maintaining said attached first and second extension rods in the longitudinal axes of said first and second surgical screws, wherein said connection with said first and second sliding retainers is facilitated by the pivoting of said first and second sliding retainers.

16. A spinal support coupling device as claimed in claim 11, wherein said locking mechanisms on said first and second sliding retainers are engaged, when said first and second sliding retainers are at a position along said first and second extension rods, such that the distance between said first sliding retainer and said first screw head at coupling rod connection point P1 and said second sliding retainer and said second screw head at coupling rod connection point P2 is equal to the length of said traveling arm (L).

17. A spinal support coupling device as claimed in claim 5, wherein said spinal support coupling device further comprises a piercing arm, coupled to the end of said traveling arm, distal to said center pivot hinge.

18. A spinal support coupling device as claimed in claim 17, wherein said piercing arm and said traveling arm are an integrally molded unit.

19. A spinal support coupling device as claimed in claim 17, wherein said piercing arm and said traveling arm are formed as separate units.

20. A spinal support coupling device as claimed in claim 17, wherein said piercing arm is curved such that it lies within an arc defined by a circle with a radius (L).

21. A spinal support coupling device as claimed in claim 20, further comprising a coupling rod, removably attached to the end of said piercing arm.

22. A spinal support coupling device as claimed in claim 21, wherein said coupling rod is curved such that it lies within an arc defined by a circle with a radius (L).

23. A spinal support coupling device as claimed in claim 21, wherein said coupling rod is configured to be guided by said piercing arm, via said traveling arm, by swinging said traveling arm around said center pivot hinge, such that said coupling rod passes through said first and second bore holes of said first and second surgical screws.

24. A spinal support coupling device as claimed in claim 23, wherein said coupling rod is released from said piercing arm after said coupling rod is in place in said bore holes, and said piercing arm is removed by rotating traveling arm back, away from said surgical screws.

25. A spinal support coupling device as claimed in claim 23, wherein after said coupling rod is in place it is secured in said bore holes of said first and second surgical screws by tightening said first and second screw heads.

26. A spinal support coupling device as claimed in claim 1, wherein said first and second pivot hinge connecting arms are independently hingedly attached to said center pivot hinge, and are independently movable with respect to one another.

27. A spinal support coupling device as claimed in claim 1, wherein said first and second pivot hinge connecting arms are independently fixedly attached to said center pivot hinge, and are disposed at fixed angles with respect to one another.

28. A spinal support coupling device as claimed in claim 1, wherein said first and second radial frame connecting arms are coupled to said first and second pivot hinge connecting arms, respectively, at points distal to said center pivot hinge.

29. A spinal support coupling device as claimed in claim 28, wherein said first and second radial frame connecting arms are fixedly attached to said first and second pivot hinge connecting arms, respectively, such that they remain at a fixed angle with respect to one another.

30. A spinal support coupling device as claimed in claim 28, wherein said first and second radial frame connecting arms are hingedly attached to said first and second pivot hinge connecting arms, respectively, so as to be freely moveable with respect to one another.

31. A spinal support coupling device as claimed in claim 29, wherein said first and second radial frame connecting arms fixedly attached to said first and second radial frames at a fixed angle in relation to one another.

32. A spinal support coupling device as claimed in claim 28, wherein said first and second radial frame connecting arms are hingedly attached to said first and second radial frames, and are capable of independent movement with respect to one another.

33. A spinal support coupling device as claimed in claim 1, wherein said first pivot hinge connecting arm, said first radial frame connecting arm and said first radial frame are each hingedly attached to each other as first element and said second pivot hinge connecting arm, said second radial frame connecting arm and said second radial frame are each hingedly attached to each other as second element wherein said first and second elements are independently hingedly attached to said center pivot hinge.

34. A spinal support coupling device as claimed in claim 1, wherein said first pivot hinge connecting arm, said first radial frame connecting arm and said first radial frame are each fixedly attached to each other as a first element and said second pivot hinge connecting arm, said second radial frame connecting arm and said second radial frame are each fixedly attached to each other as a second element wherein said first and second elements are independently hingedly attached to said center pivot hinge.

35. A spinal support coupling device as claimed in claim 1, wherein said first and second pivot hinge connecting arms, said first and second radial frame connecting arms and said first and second radial frames are each fixedly attached to each other as single continuous element, hingedly attached to said center pivot hinge.

36. A spinal support coupling device as claimed in claim 1, wherein when said first and second radial frames are attached to said first and second extension rods, said first and second pivot hinge connecting arms extend downward such that lines, drawn between said center point at said center pivot hinge to said first and second surgical screw bores at coupling rod connection points P1, P2, pass thought the longitudinal axes of said first and second pivot hinge connecting arms.

37. A spinal support coupling device, as claimed in claim 1, wherein said device is constructed of any one of surgical grade stainless steel, titanium, rigid polyurethane and plastic.

* * * * *